(12) United States Patent
Murphy et al.

(10) Patent No.: US 6,752,791 B2
(45) Date of Patent: Jun. 22, 2004

(54) NEEDLE CONTROL DEVICE

(75) Inventors: Kieran P. J. Murphy, Baltimore, MD (US); Christopher G. Dixon, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 0 days.

(21) Appl. No.: 10/285,889

(22) Filed: Nov. 1, 2002

(65) Prior Publication Data

US 2003/0106607 A1 Jun. 12, 2003

Related U.S. Application Data

(63) Continuation-in-part of application No. 09/594,151, filed on Jun. 15, 2000, now Pat. No. 6,488,667.

(51) Int. Cl.[7] .......................... A61M 5/32; A61M 5/00
(52) U.S. Cl. .................. 604/272; 604/173; 604/177; 604/264
(58) Field of Search ............................. 604/272, 264; 606/167–187

(56) References Cited

U.S. PATENT DOCUMENTS

| | | |
|---|---|---|
| 4,177,797 A | 12/1979 | Baylis et al. |
| 4,485,815 A | 12/1984 | Amplatz et al. |
| 4,733,661 A | 3/1988 | Palestrant |
| 4,798,213 A | 1/1989 | Doppelt |
| 5,290,266 A | 3/1994 | Rohling et al. |
| 5,758,655 A | 6/1998 | Como Rodriguez et al. |
| 5,928,238 A | 7/1999 | Scarborough et al. |
| 6,022,324 A | 2/2000 | Skinner |
| 6,033,411 A | 3/2000 | Preissman |
| 6,488,667 B1 * | 12/2002 | Murphy ...................... 604/272 |

OTHER PUBLICATIONS

Percutaneous Vertebroplasty for Osteolytic Metastases and Myeloma: Effects of the Percentage of Lesion Filling and the Leakage of Methyl Methacrylate at Clinical Follow–up; Anne Cotten, M.D. et al.; Radiology; Aug., 1996; pp. 525–530.

Percutaneous Vertebroplasty: State of the Art; Anne Cotten, M.D. et al; Scientific Exhibit, vol. 18, No. 2, Mar.–Apr. 1998; pp. 311–323.

* cited by examiner

Primary Examiner—Brian L. Casler
Assistant Examiner—Roz Maiorino
(74) Attorney, Agent, or Firm—Richard J. Godlewski

(57) ABSTRACT

An apparatus for holding a needle such as a medical needle, during exposure to radiation, such as X-ray radiation. The apparatus includes a needle collar and a control bar. The needle collar attaches to the needle shaft and has a first attachment point while the control bar has a second attachment point, where the first and second attachment points cooperate to releasably engage the needle collar and the control bar. In use, when the needle collar and the control bar are engaged, the user grasps the control bar to control the needle while releasing the needle and maintaining the hands of the user outside of a field of the radiation, e.g., outside of a field of the X-ray radiation. The control bar is dimensioned such that its proximal end (i.e., the end to be grasped by the user) is outside the field of radiation.

5 Claims, 4 Drawing Sheets

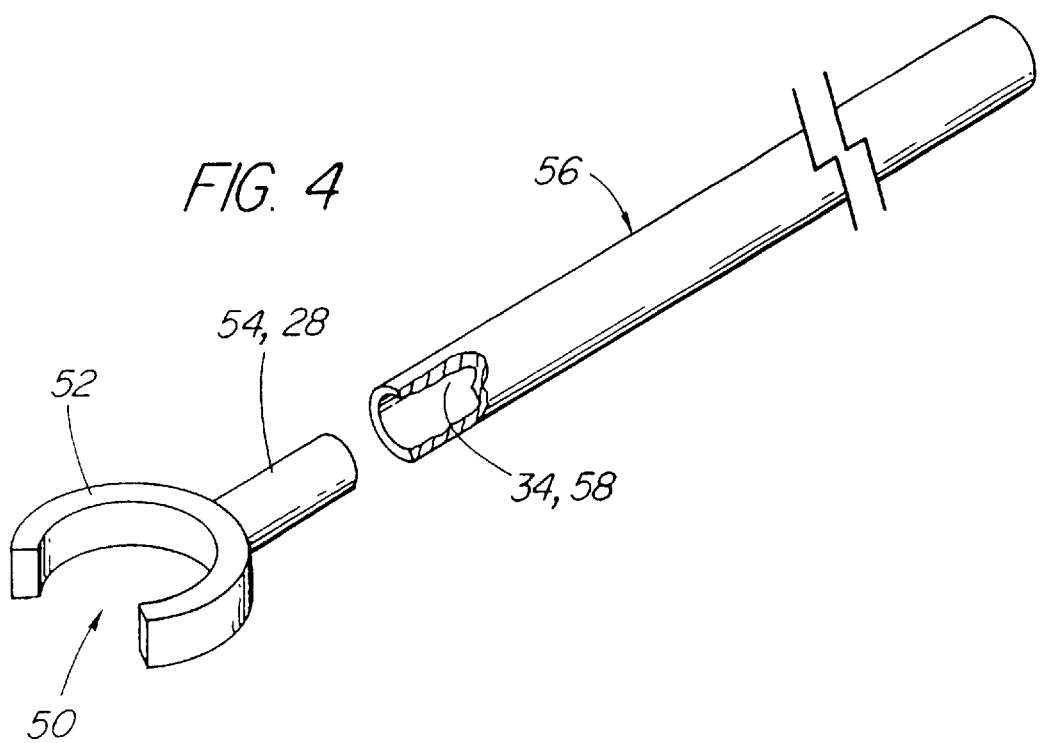

NEEDLE CONTROL DEVICE

RELATED APPLICATION INFORMATION

This is a continuation-in-part application of U.S. patent application Ser. No. 09/594,151 filed Jun. 15, 2001 now U.S. Pat. No. 6,488,667.

TECHNICAL FIELD

This relates to a medical device and more particularly to a needle control device to obviate or mitigate exposure of excessive radiation to the hand of a user.

BACKGROUND OF THE INVENTION

Several medical treatments involve the use of needles and continuous applied doses of radiation while a medical practitioner is within the range of the radiation. An example of such a procedure is vertebroplasty.

Percutaneous vertebroplasty involves the injection of a bone cement or other suitable biomaterial into a vertebral body via a percutaneous route under X-ray guidance. The cement is injected as a semi-liquid substance through a needle that has been passed into the vertebral body, generally along a transpedicular or posterolateral approach.

Percutaneous vertebroplasty is intended to provide structural reinforcement of a vertebral body through injection, by a minimally invasive percutaneous approach, of bone cement into the vertebral body. See, for example, Cotten, A., et al "Percutaneous vertebroplasty: State of the Art." *Radiographics* 1998 March–April; 18(2):311–20; discussion at 320–3. Percutaneous vertebroplasty can result in increased structural integrity, decreased micromotion at the fracture site and possibly a destruction of pain fibers due to the heat of the bone cement as it polymerizes and sets. Complete pain relief can be achieved in up to 80% of patients.

Generally, when performing vertebroplasty, a needle of an appropriate gauge (such as 11 gauge or 13 gauge in a smaller vertebral body) is passed down the pedicle until it enters the vertebral body and reaches the junction of the anterior and middle thirds. Great skill is usually required to insert the needle at a suitable angle and pass the needle through the periosteum, down the pedicle and into the vertebral body. A suitable cement is prepared and injected through the needle and into the vertebral body, under lateral X-ray projection fluoroscopy imaging. The injection is stopped as the cement starts to extend into some unwanted location such as the disc space or towards the posterior quarter of the vertebral body, where the risk of epidural venous filing and hence spinal cord compression is greatest. The injection is also discontinued if adequate vertebral filling is achieved.

The procedure usually requires the user (typically a physician) to hold the needle in position while (at least a portion of) the body is being radiated. This is normally needed since the needle should be stabilized and oriented in the correct position in order for the intended target in the body to be reached. This protocol leads to the creation of a field of radiation within which the user's hands typically are placed. Consequently, the user will received repeated doses of radiation which can lead to one or more occupational health hazards (e.g., health problems) and/or can shorten the career of the user due to the user receiving quantities of radiation beyond the allowable limits.

Accordingly, there is a need in the art for a means by which radiative medical procedures such as percutaneous vertebroplasty may be performed while obviating or mitigation the deleterious effects of exposure of the physician or other user to excessive radiation.

SUMMARY OF THE INVENTION

It is an object of the present invention to provide a novel needle control device for holding a needle that obviates or mitigates at least one of the disadvantages of the prior art.

Accordingly, in one of its aspects, the present invention provides an apparatus for control of a needle (i.e., a needle control device) used in a field of radiation, the apparatus comprising:
 a needle collar for attachment to the needle, the needle collar comprising a first attachment point; and
 as control bar having a second attachment point, the first attachment point and the second attachment point cooperating to releasably engage the needle collar and the control bar.

In another of its aspects, the present invention provides a needle comprising:
 a handle;
 a cannula attached to the handle;
 a needle collar attached to the needle, the needle collar comprising a first attachment point; and
 a control bar having a second attachment point, the first attachment point and the second attachment point cooperating to releasably engage the needle collar and the control bar.

In yet another of its aspects, the present invention provides a kit of parts comprising:
 a needle comprising: a handle; a cannula attached to the handle; a needle collar attached to the needle, the needle collar comprising a first attachment point; and
 a control bar having a second attachment point, the first attachment point and the second attachment point cooperating to releasably engage the needle collar and the control bar.

Thus, the present invention is an apparatus for a physician to safely hold a needle, during exposure of the treatment site and the needle to radiation, such as X-ray radiation. The apparatus includes a needle collar and a control bar. The needle collar attaches to the needle and has a first attachment point. The control bar has a second attachment point. The first attachment point and the second attachment point cooperate to releasably engage the needle collar and the control bar. In use, the needle collar and the control bar are engaged and the user grasps the control bar to control the needle are engaged and the user grasps the control bar to control the needle while maintaining the hands of the user outside of a field of the radiation, e.g., outside of a field of the X-ray radiation. The control bar is dimensioned such that its proximal end (i.e., the end to be grasped by the user) is outside of the field of radiation.

BRIEF DESCRIPTION OF THE DRAWING

FIG. 4 shows an alternative needle collar and control bar.

DETAILED DESCRIPTION

Figure 1:
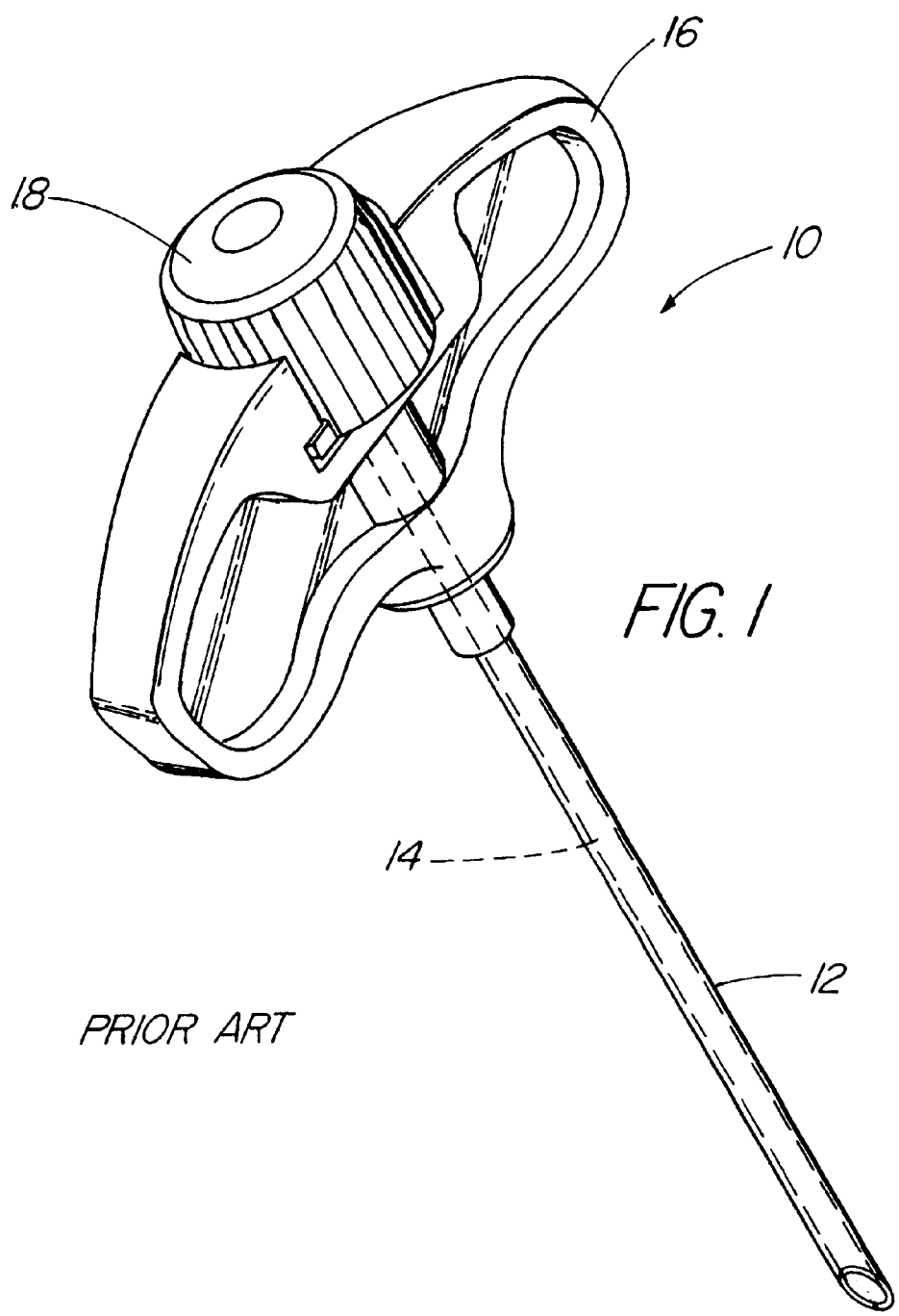
FIG. 1 illustrates an isometric view of a PRIOR ART vertebroplasty needle.

Before discussing the specific embodiments of the invention, a needle suitable for use with the needle control device will be described with reference to FIG. 1. A vertebroplasty needle is indicated generally at 10 and is preferably used for expressing bone cement or a suitable biomaterial into a vertebral body. For vertebroplasty, it is preferred that needle 10 be constructed of surgical stainless steel, although those of skill in the art will appreciate that needle 10 may be constructed of any other suitable materials. Vertebroplasty needle 10 generally consists of a cannula (also referred to as a sheath or a trocar) 12 and an insert 14 receivably removable within the sheath. Cannula 12 has a handle 16 for grasping by an operator. Insert 14 has a connector 18 operable to releasably attach to handle 16. Insert 14 is receivable within cannula 12 for insertion of needle 10 into a vertebral body via percutaneous routes. Insert 14 is removable from cannula 12 to allow for a conventional injector (not shown), suitable for cement delivery, to be releasably attached to handle 16 to facilitate the injection of cement through cannula 12 into a vertebral body. The injector can be a syringe or a cement delivery needle or other suitable injector as will occur to those of skill in the art.

Figure 2:
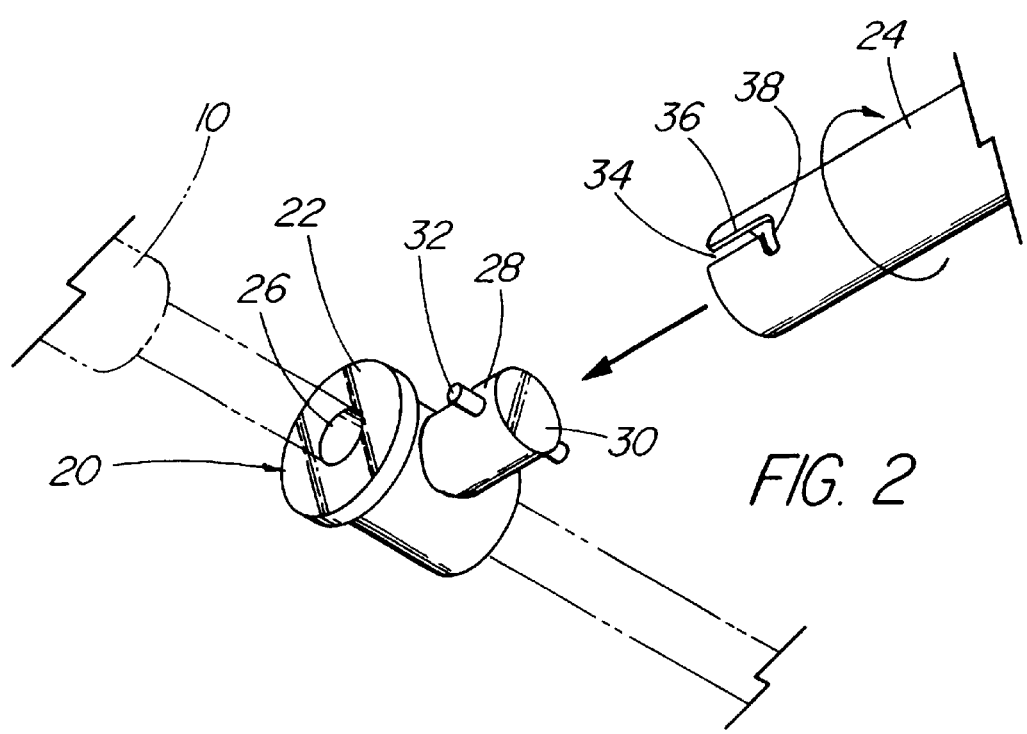
FIG. 2 illustrates an isometric view of a portion of the present needle control device with the control bar removed.
Figure 3:
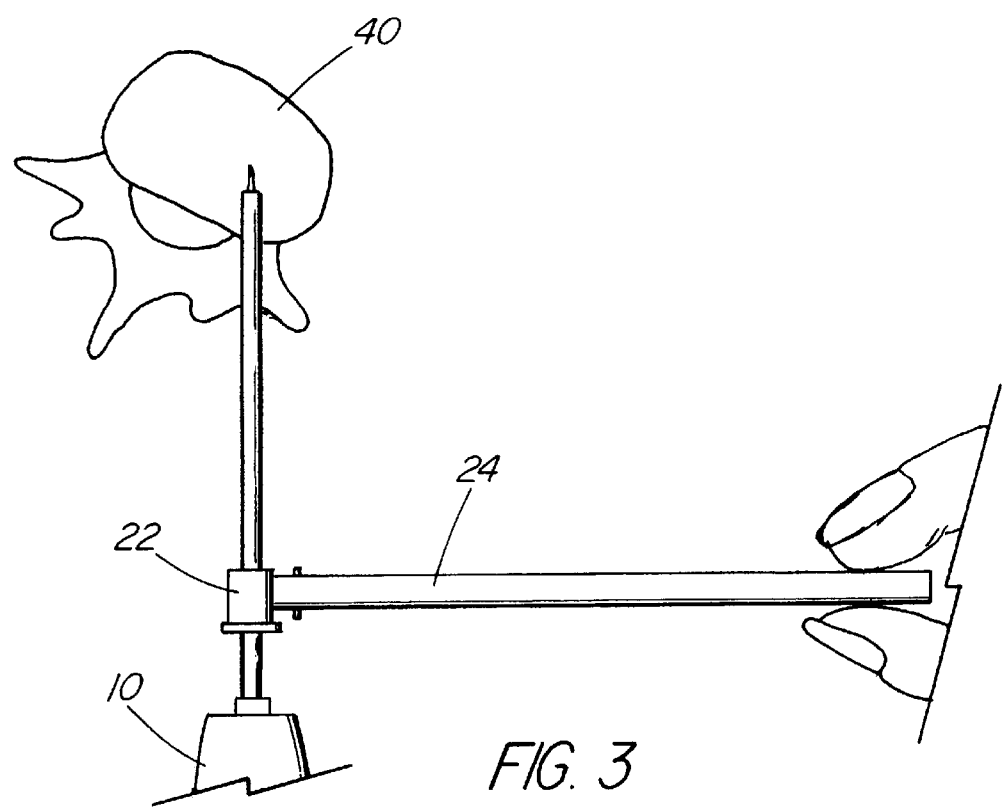
FIG. 3 illustrates an isomeric schematic view of the present needle control device in use.

Referring now to FIGS. 2 and 3, a needle control device for holding a needle is indicated generally at 20. Device 20 includes a needle collar 22 that is releasably attachable to a control bar 24.

In a presently preferred embodiment, needle collar 22 has an opening 26 for releasably engaging with needle 10 when needle 10 is passed through opening 26. Needle collar 22 may preferably serve as a depth marker and may be made from medical grade plastic or from other suitable materials. Other embodiments of needle collar 22 will occur to those of skill in the art, such as depth markers that include a gasket which can be constricted or loosened about the needle in order to adjust the grip of the depth marker on the needle. The interior diameter of opening 26 in needle collar 22 is slightly larger than the exterior diameter of needle 10, and the size and material of needle collar 22 cooperates to create a friction or interference fit around needle 10. Other suitable depth markers can be used.

Needle collar 22 has a first attachment point 28. First attachment point 28 protrudes from needle collar 22 and is operable to connect with control bar 24. In a first embodiment, first attachment point 28 comprises a post 30 with a pair of bosses 32 substantially perpendicular to post 30.

Control bar 24 is made from medical grade plastic or other suitable materials can be used. Preferably, control bar 24 is radiolucent, so as not to interfere with the X-ray image. Control bar 24 is operable to connect with first attachment point 28. In a presently preferred embodiment, control bar 24 has a second attachment point 34 that releasably engages with first attachment point 28. Second attachment point 34 is seen to be a female receptacle or cavity to receive post 30 thereinto, and that has a pair of axially extending slots 36 and a pair of recesses 38, extending laterally from respective slots 36. Recesses 38 are substantially perpendicular to each slot 36 to releasably retain a respective boss 32. Recesses 38 extend substantially in opposite directions, so that when control bar 24 is twisted each boss 32 is received and retained within its respective slot 36.

Preferably, control bar 24 is from about 10 cm to about 40 cm in length. More preferably, control bar 24 is between about 20 to 30 cm in length. It will be understood, however, that the length of control bar 24 may vary depending on the size of the needle that is used and the medical process in which it is being used. In particular, the length of control bar 24 is chosen to ensure that it can be grasped in a position that is outside the field of radiation generated during the procedure.

The operation of device 20 will now be described with reference to the foregoing and to FIG. 3. More specifically, a method for performing vertebroplasty in accordance with an embodiment of the invention, will now be discussed, utilizing a needle 10 and needle control device 20 and performed on a patient having a vertebra 40. The patient would be placed in the prone position so that vertebra 40 is within the radiation field generated by an imaging device (not shown). In most such cases, the imaging device is an X-ray projection fluoroscopy imaging device.

Needle 10 is inserted into the vertebral body of the patient. Bar 24 is attached to needle 10 by post 30 being received into female end 34 of control bar 24 with bosses 32 engaging in axially extending slots 36 and rotating control bar 24 until bosses 32 are releasably engaged in laterally extending recesses 38 in communication with slots 36. Control bar 24 is oriented to position the user's hand outside of the field of X-ray radiation. Control bar 24 is grasped by the user, who then may release the needle while maintaining positional control thereover by control bar, and the X-ray device is turned on and an image is taken. The X-ray only exposes the vertebral body, the needle and the adjacent portions of the needle control device.

While the embodiments discussed herein are directed to particular implementations of the present invention, it will be apparent that variations to these embodiments are within the scope of the invention. For example, needle control device 20 can be made from any material that is suitable for surgical procedures and is radiolucent.

Further, it is contemplated, as seen in FIGS. 2 and 3, that first attachment point 28 can be a male luer lock and second attachment point 34 can be a female luer lock (or vice versa). Alternatively, first attachment point 28 can be a male luer slip and second attachment point 34 can be a female luer slip (or vice versa).

Another embodiment of the needle control device of the present invention is disclosed in FIG. 4. Needle collar 50 is shown having a C-shaped needle-clamping section 52 whereby the collar may be slipped over the needle (prior to beginning the vertebroplasty procedure) from the needle's distal end (not shown) until it is positioned at the desired location, such as to denmark a selected insertion depth by the collar's distal most side. The inside diameter of needle-clamping section 52 is preferably selected to be incrementally smaller than the outside diameter of the shaft of the needle with which it is to be used, therefore providing for a force fit to self-retain on the needle shaft. Cylindrical protrusion 54 extends laterally from collar 50 to define a male first attachment point 28. Control bar 56 is shown to be an elongate member having a second attachment point 34 defined in a female cavity 58 complementary to protrusion 54 and thereby be adapted to releasably and detachable receive protrusion 54 thereinto in a force fit. The force fit can easily be defined by the protrusion having an outside diameter selected to be incrementally larger than the inside diameter of the female cavity 58, and can be of sufficient force to avoid inadvertent detachment but be easily overcome manually for desired detachment by axial pulling of the control bar away from the needle without resulting in undesirable movement of the needle relative to the patient. Both collar 50 and control bar 56 can for example be extruded and/or molded of plastic material such as, for example, polyethylene or nylon.

The present invention provides a novel needle control device for holding a needle during exposure to radiation, such as X-ray radiation. Of course, those of skill in the art will recognize that the present needle control device has a number of applications and uses in image guided procedures (e.g., magnetic resonance imaging (MRI) and the like). The device includes a needle collar for retaining the needle and a control bar for allowing the user to hold the needle in position prior to and/or during and/or after the X-ray process. The needle collar includes a first attachment point that, preferably, is complementary to a second attachment point positioned on the bar for releasable attachment to the control bar. The control bar allows the user to maintain control over the needle while taking an X-ray image and avoid exposing the user to the excessive X-ray radiation.

While the present invention has been described with reference to preferred and specifically illustrated embodiments, it will of course by understood by those skilled in the arts that various modifications to these preferred and illustrated embodiments may be made without departing from the spirit and scope of the invention.

All publications, patents and patent applications referred to herein are incorporated by reference in their entirety to the same extend as if each individual publication, patent or patent application was specifically and individually indicated to be incorporated by reference in its entirety.

What is claimed is:

1. An apparatus for control of a needle used in a field of radiation, the apparatus comprising:

a needle collar for attachment to the needle, the needle collar comprising a first attachment point; and a control bar having a second attachment point, the first attachment point and the second attachment point cooperating to releasably engage the needle collar and the control bar, wherein the needle collar comprises a C-shaped needle-engaging section having an inner diameter selected to establish a snug fit with the needle to self-retain thereonto.

2. An apparatus for control of a needle used in a field of radiation, the apparatus comprising:

a needle collar for attachment to the needle, the needle collar comprising a first attachment point; and a control bar having a second attachment point, the first attachment point and the second attachment point cooperating to releasably engage the needle collar and the control bar, wherein the first attachment point is a protuberance extending radially from the needle collar and having a selected outer diameter, and the second attachment point is a female cavity at an end of the control bar and having an inside diameter selected to establish a force fit with said protuberance upon receipt of said protuberance thereinto.

3. A needle comprising:

a handle;

a cannula attached to the handle;

a needle collar attached to the needle, the needle collar comprising a first attachment point; and a control bar having a second attachment point, the first attachment point and the second attachment point cooperating to releasably engage the needle collar and the control bar, wherein the needle collar comprises a C-shaped needle-engaging section having an inner diameter selected to establish a snug fit with the needle to self-retain thereonto.

4. A needle comprising:

a handle;

a cannula attached to the handle;

a needle collar attached to the needle, the needle collar comprising a first attachment point; and a control bar having a second attachment point, the first attachment point and the second attachment point cooperating to releasably engage the needle collar and the control bar, wherein the first attachment point is a protuberance extending radially from the needle collar and having a selected outer diameter, and the second attachment point is a female cavity at an end of the control bar and having an inside diameter selected to establish a force fit with said protuberance upon receipt of said protuberance thereinto.

5. A needle comprising:

a handle;

a cannula attached to the handle;

a needle collar attached to the needle, the needle collar comprising a first attachment point; and a control bar having a second attachment point, the first attachment point and the second attachment point cooperating to releasably engage the needle collar and the control bar, wherein the needle collar and the control bar are releasably engagable for the control bar and the needle to be in a substantially perpendicular orientation.

* * * * *